(12) United States Patent
Tong

(10) Patent No.: US 12,161,333 B2
(45) Date of Patent: Dec. 10, 2024

(54) WOUND CLOSURE DEVICE AND CONNECTING UNIT

(71) Applicant: SHANGHAI JINCHEN MEDICAL & PHARMACEUTICAL TECHNOLOGY CO., LTD., Shanghai (CN)

(72) Inventor: Huijin Tong, Shanghai (CN)

(73) Assignee: Shanghai Jinchen Medical & Pharmaceutical Technology Co., Ltd., Shanghai (CN)

( * ) Notice: Subject to any disclaimer, the term of this patent is extended or adjusted under 35 U.S.C. 154(b) by 533 days.

(21) Appl. No.: 17/605,459

(22) PCT Filed: Apr. 14, 2020

(86) PCT No.: PCT/CN2020/084733
§ 371 (c)(1),
(2) Date: Oct. 21, 2021

(87) PCT Pub. No.: WO2020/216103
PCT Pub. Date: Oct. 29, 2020

(65) Prior Publication Data
US 2022/0211378 A1    Jul. 7, 2022

(30) Foreign Application Priority Data
Apr. 24, 2019   (CN) .......................... 201910334049.3

(51) Int. Cl.
*A61B 17/08* (2006.01)
(52) U.S. Cl.
CPC ...... *A61B 17/085* (2013.01); *A61B 2017/088* (2013.01)
(58) Field of Classification Search
None
See application file for complete search history.

(56) References Cited

U.S. PATENT DOCUMENTS 5,693,068 A * 12/1997 Kuhlman ............ A61F 13/0259
604/304
6,126,615 A * 10/2000 Allen ..................... A61B 10/02
600/562

(Continued)

FOREIGN PATENT DOCUMENTS

| CN | 101843507 A | 9/2010 |
|---|---|---|
| CN | 105286935 A | 2/2016 |

(Continued)

OTHER PUBLICATIONS

English abstract of CN101843507A.

(Continued)

*Primary Examiner* — Tan-Uyen T Ho
*Assistant Examiner* — David P Stein
(74) *Attorney, Agent, or Firm* — Caesar Rivise, PC

(57) ABSTRACT

The present invention discloses a wound closure device and a connecting unit, which belongs to the field of medical products, aiming at solving the problems of high cost, long period and difficult mass production of existing wound closure devices manufactured according to the shape and size of a wound. The connecting unit of the present invention is structured as an independent connecting unit which can be mass produced, when a wound with a specific shape and size is to be treated, a wound closure device structure suitable for the wound can be formed simply by selecting corresponding size and number of connecting units, and assembling the same correspondingly, therefore, the present invention can effectively reduce the production cost by means of mass production not depending on specific shape and size of a wound. In addition, a plurality of connecting units are connected correspondingly to form a structurally stable window, avoiding failure of the window caused by deformation when a wound is closed by a closure device.

11 Claims, 10 Drawing Sheets

(56) References Cited

U.S. PATENT DOCUMENTS

| | | | |
|---|---|---|---|
| 10,874,395 B2 | 12/2020 | Nezu | |
| 2012/0016410 A1* | 1/2012 | Belson | A61B 17/085 606/213 |
| 2019/0076145 A1 | 3/2019 | Belson et al. | |
| 2021/0267597 A1 | 9/2021 | Zhang et al. | |

FOREIGN PATENT DOCUMENTS

| | | |
|---|---|---|
| CN | 107822682 A | 3/2018 |
| CN | 109124712 A | 1/2019 |
| CN | 109152574 A | 1/2019 |
| CN | 210249948 U | 4/2020 |

OTHER PUBLICATIONS

English abstract of CN105286935A.
English abstract of CN107822682A.
English abstract of CN210249948U.
International Search Report for corresponding PCT Application No. PCT/CN2020/084733 dated Jul. 16, 2020.

* cited by examiner

WOUND CLOSURE DEVICE AND CONNECTING UNIT

CROSS-REFERENCE TO RELATED APPLICATIONS

This application is a U.S. National Phase Application of PCT/CN2020/084733, filed Apr. 14, 2020, which claims priority to CN 201910334049.3, filed Apr. 24, 2019, the contents of which applications are incorporated herein by reference in their entireties for all purposes.

FIELD OF THE INVENTION

The present invention relates to the field of medical products, in particular to a wound closure device and a connecting unit.

BACKGROUND OF THE INVENTION

Chinese Patent Application No. CN201811101842.0 discloses a "wound closure device" (hereinafter referred to as Document 1), by which a wound healing area corresponding to the position of a wound can be formed to construct a complete or independent undisturbed healing area, so as to facilitate the treatment and healing of the wound.

In Document 1, a window is correspondingly formed by structurally enclosing an isolation fence and is connected to a fixator through a closure device, when using the window, the closure device will apply a pulling force between the window and the fixator, so as to apply a pulling force to the wound, then draw and close the wound. Therefore, the window should be of a fixed shape to bear certain pulling force. In Document 1, the window part (specifically, the wall of the window) should be of a shaped structure, e.g. a structure provided with a prefabricated plastic part. However, the shape and size of a wound are often unknown in advance, if each wound needs to be specially prefabricated according to the shape and size of the wound before it can be made into the required wound closure device, which greatly limits the use of the wound closure device. Moreover, a wound closure of a specific size is specially customized according to the shape and size of the wound, which has the problems of high cost, long period and difficult mass production.

SUMMARY OF THE INVENTION

The present invention intends to solve the technical problems of high cost, long period and difficult mass production of existing wound closure devices manufactured according to the shape and size of a wound.

A technical solution for solving the technical problem in the present invention is a connecting unit, which includes a cofferdam baffle, a closure device and a fixator, one end of the closure device is connected to the fixator and the other end thereof is connected to the back side of the cofferdam baffle, a fixed adhesive surface for attaching to skin is provided on the bottom surface of the fixator, left and right ends of the cofferdam baffle are connecting ends, a first connecting part is arranged at one connecting end of the cofferdam baffle and a second connecting part is arranged at the other connecting end thereof, the first connecting part and the second connecting part are corresponding mating structures capable of adjusting and locking the connecting angle θ.

Furthermore, the first connecting part is a polygonal prism and the second connecting part is a polygonal hole consistent with the polygonal prism; alternatively, the first connecting part is a plurality of positioning posts and the second connecting part is a plurality of positioning holes in fit with the positioning posts in a misaligned manner.

Furthermore, the corresponding mating structure of the first connecting part and the second connecting part is an articulated connection structure, at which a locking mechanism is provided.

Furthermore, the locking mechanism is a screw or a ratchet and ratchet wheel mechanism.

Furthermore, the connecting unit further includes a limiting connecting rod, and the corresponding mating structure of the first connecting part and the second connecting part is an articulated connection structure; the cofferdam baffle is provided with at least one limiting slot arranged at intervals along the connecting direction of the cofferdam baffle; and an end of the limiting connecting rod is provided with a chuck in correspondingly clamping fit with the limiting slot.

Furthermore, the limiting slot and the chuck are of an articulated mating structure, and the limiting connecting rod is I-shaped, Y-shaped or X-shaped.

Furthermore, the limiting slot and the chuck are of a directional mating structure.

Furthermore, one end of the limiting slot penetrates out from an upper end of the cofferdam baffle.

Furthermore, the closure direction of the closure device is perpendicular to the cofferdam baffle, a plurality of closure devices are provided, the plurality of closure devices are arranged at intervals along the connecting direction of the cofferdam baffle; the closure device is of a ratchet structure or a lacing structure; a base band parallel to the cofferdam baffle is provided on the edge of the fixator facing the side of the cofferdam baffle.

In addition, the present invention further provides a wound closure device formed by combining the connecting units, a plurality of connecting units are provided, the plurality of connecting units are sequentially connected through the connecting ends of the cofferdam baffle and then enclosed to form an annular closed window, and the closure device and the fixator in each of the connecting units are located at the periphery of the window.

Furthermore, functional modules are provided within the internal space of the window, and are at least one of an alignment reference support module, a wound exudate absorption module, a wound hemostasis module, a wound bacteriostasis and antibacterial module, a wound information acquisition module and a cell tissue regeneration module, wherein a bottom surface, facing a wound, of the alignment reference support module is a rigid reference plane.

Furthermore, the wound closure device further includes a peripheral sealing film and an internal sealing film, wherein the peripheral sealing film correspondingly covers the periphery of the window and is provided with an opening corresponding to the window, the internal sealing film correspondingly covers the window, and the edge of the internal sealing film fits over an edge corresponding to the opening of the peripheral sealing film in a sealing manner, so as to form a negative pressure sealing chamber in an area covered by the peripheral sealing film and the internal sealing film.

Furthermore, the wound closure device further includes a negative pressure pipeline which communicates the negative pressure sealing chamber with the outside.

The advantageous effect of the present invention is as follows: the connecting unit of the present invention is structured as an independent connecting unit which can be mass produced in advance, when a wound with a specific shape and size is to be treated, a wound closure structure suitable for the wound can be formed simply by selecting corresponding size and number of connecting units, and assembling the same correspondingly, therefore, the present invention can effectively reduce the production cost by means of mass production not depending on specific shape and size of a wound. In addition, according to the wound closure device of the present invention, a plurality of connecting units are connected correspondingly to form a structurally stable window, avoiding failure of the window caused by deformation when a wound is closed by a closure device.

Figure 1:
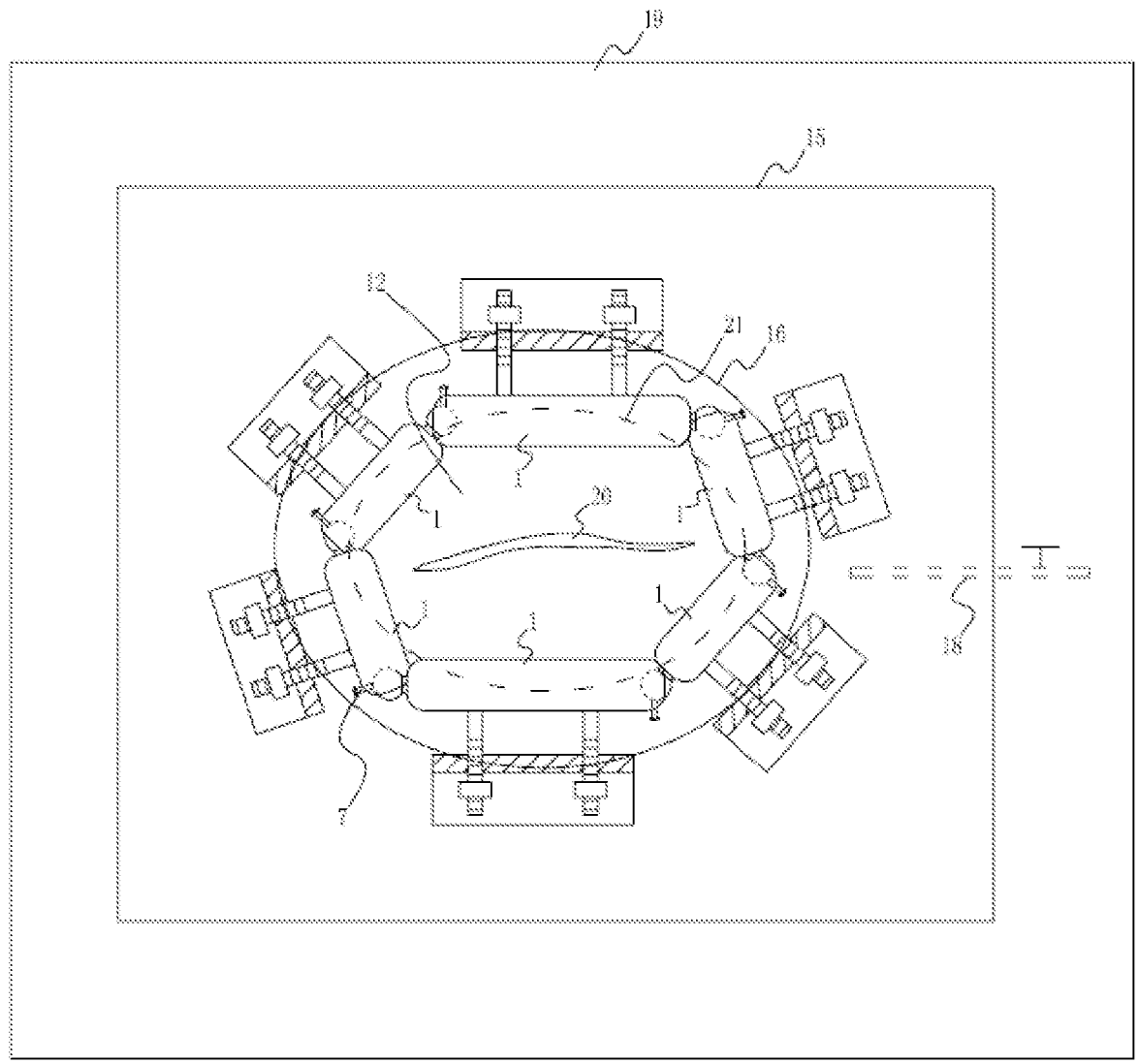
FIG. 1 is a top view of a wound closure device of the present invention when in use.

The markings in drawings are as follows: cofferdam baffle 1, closure device 2, fixator 3, fixed adhesive surface 4, first connecting part 5, polygonal prism 51, rotating shaft 52, ball 53, positioning post 54, second connecting part 6, polygonal hole 61, shaft hole 62, ball cavity 63, positioning hole 64, locking mechanism 7, screw 71, ratchet and ratchet wheel mechanism 72, ratchet wheel 721, ratchet 722, limiting connecting rod 8, limiting slot 9, chuck 10, base band 11, window 12, alignment reference support module 13, rigid reference plane 14, peripheral sealing film 15, internal sealing film 16, negative pressure sealing chamber 17, negative pressure pipeline 18, skin 19, wound 20, opening 21, U-shaped part 22.

DETAILED DESCRIPTION OF THE PREFERRED EMBODIMENTS

The present invention will be further described with reference to the attached drawings and specific embodiments.

Figure 11:
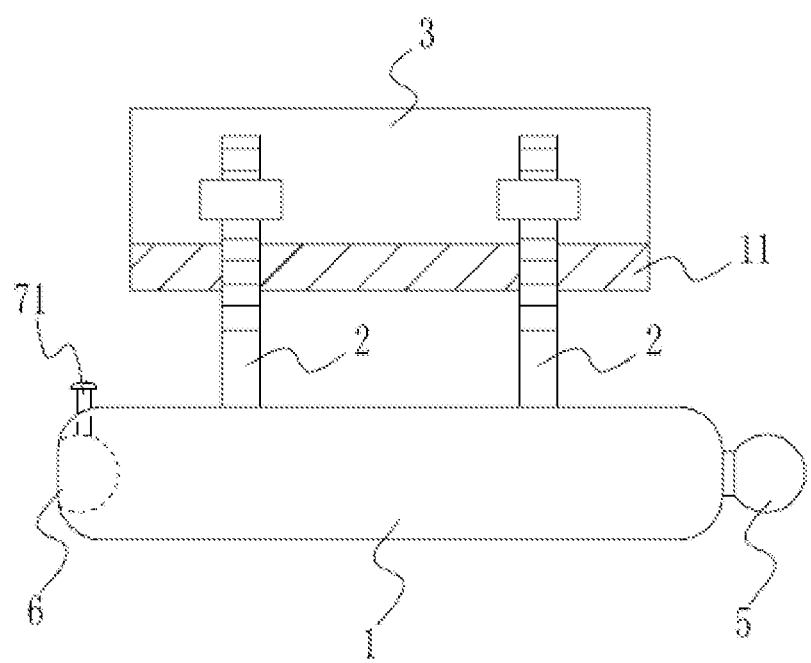
FIG. 11 is a top view of a single connecting unit according to the present invention.

As shown in FIG. 11, the connecting unit of the present invention includes a cofferdam baffle 1, a closure device 2 and a fixator 3, one end of the closure device 2 is connected to the fixator 3 and the other end thereof is connected to the back side of the cofferdam baffle 1, a fixed adhesive surface 4 for attaching to skin 19 is provided on the bottom surface of the fixator 3, left and right ends of the cofferdam baffle 1 are connecting ends, a first connecting part 5 is arranged at one connecting end of the cofferdam baffle 1 and a second connecting part 6 is arranged at the other connecting end thereof, the first connecting part 5 and the second connecting part 6 are corresponding mating structures capable of adjusting and locking the connecting angle $\theta$.

Wherein, the first connecting part 5 and the second connecting part 6 are corresponding mating structures capable of adjusting and locking the connecting angle $\theta$; meaning when two connecting units are connected, the first connecting part 5 of one of the two connecting units is in correspondingly fit connection with the second connecting part 6 of the other connecting unit, and during the connection process, the included angle $\theta$ between the cofferdam baffles 1 in the two connecting units can be adjusted, and when the included angle $\theta$ is adjusted to the required 0 value, the position relationship of the cofferdam baffles 1 of the two connecting units can be locked, that is, the angle $\theta$ can be locked. Through the above functional arrangement, the two cofferdam baffles 1 can finally form a relatively fixed connection relationship, the purpose is when a wound closure device is to be formed, a plurality of cofferdam baffles 1 can be connected sequentially to form a structurally stable window 12 which can provide a force against the closure effect of the closure device 2 on a wound, and prevent failure of the wound closure device caused by deformation of the window 12 due to the closure effect of the closure device.

Figure 12:
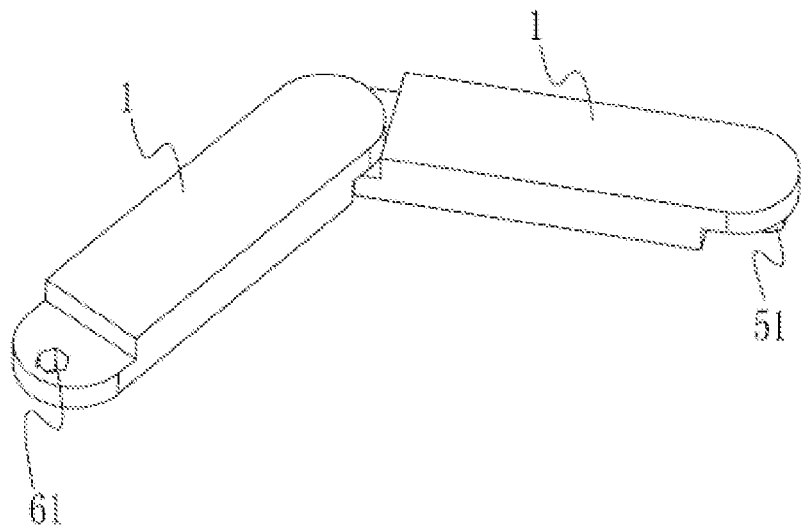
FIGS. 12 and 13 are schematic diagrams of the connecting units when the polygonal prisms are in fit with the polygonal holes.
Figure 13:
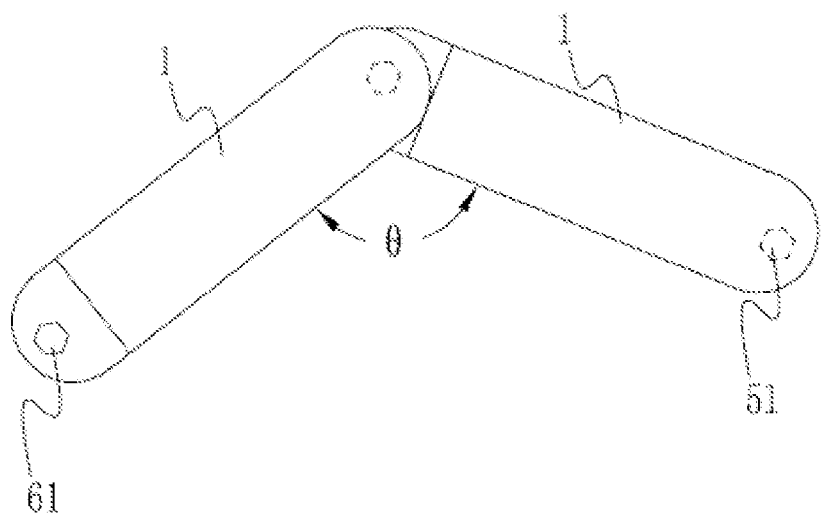

Specifically, the specific structure for achieving the function that "the first connecting part 5 and the second connecting part 6 are corresponding mating structures capable of adjusting and locking the connecting angle $\theta$" in the present invention can be at least as follows:

First, with reference to FIGS. 12 and 13, the first connecting part 5 is a polygonal prism 51, and the second connecting part 6 is a polygonal hole 61 consistent with the polygonal prism. In this way, the required function can be realized through the cooperation of the polygonal prism 51 and the polygonal hole 61. Moreover, the adjustable angle $\theta$ between the polygonal prism 51 and the polygonal hole 61 is determined theoretically by the number of sides of the polygonal prism 51. For example, i.e., when the polygonal prism 51 shown in FIGS. 12 and 13 is a regular hexagonal prism, the adjustable angle is a multiple of 60°; similarly, when the polygonal prism 51 is a regular dodecagon, the adjustable angle is a multiple of 30°.

Figure 20:
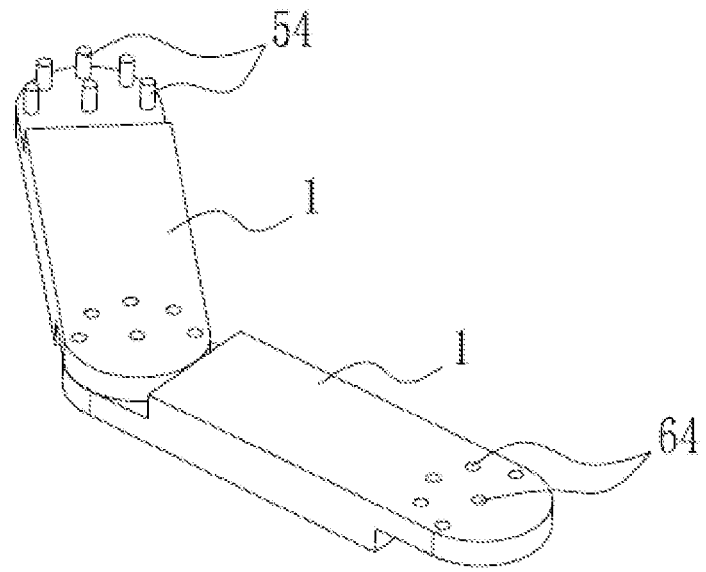
FIGS. 20 and 21 are schematic diagrams of the connecting units when a plurality of positioning posts are in fit with a plurality of positioning holes.
Figure 21:
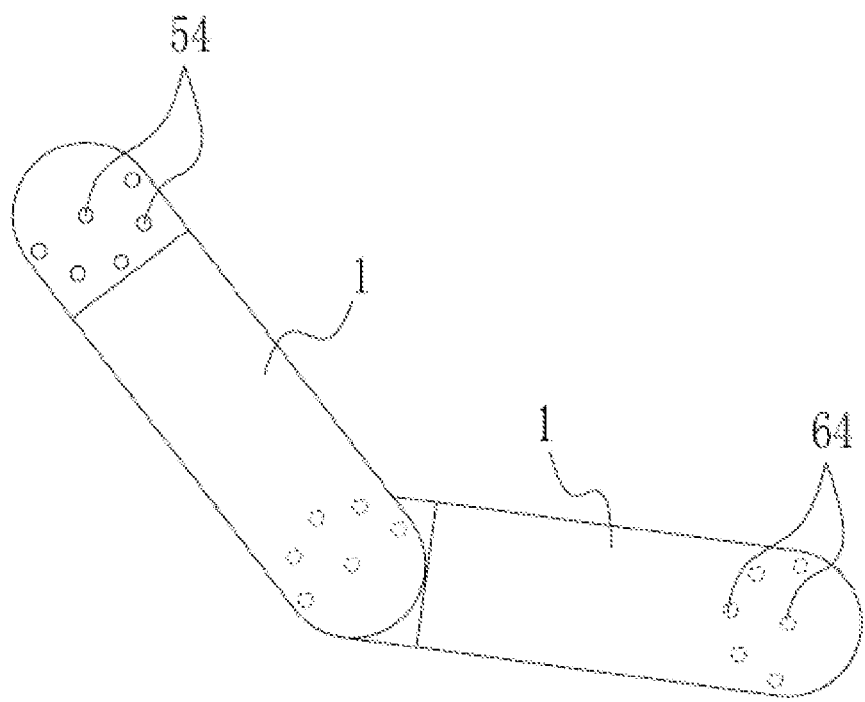

Secondly, with reference to FIGS. 20 and 21, the two first connecting parts 5 are a plurality of positioning posts 54, and the second connecting parts 6 are a plurality of positioning holes 64 in fit with the positioning posts 54 in a misaligned manner. The misaligned fit means, when rotating relatively for a certain angle, the two cofferdam baffles 1 can be connected through at least two positioning posts 54 and two positioning holes 64, this structure can also realize the above required functions. As shown, the plurality of positioning posts 54 and the plurality of positioning holes 64 can be arranged at uniform intervals along the circumferential direction, and one positioning post 54 and one positioning hole 64 can be arranged in the middle of the circumference, with such an arrangement, the angle θ can be adjusted theoretically as an integral multiple of the included angle between two adjacent positioning posts 54 on the circumference.

Figure 14:
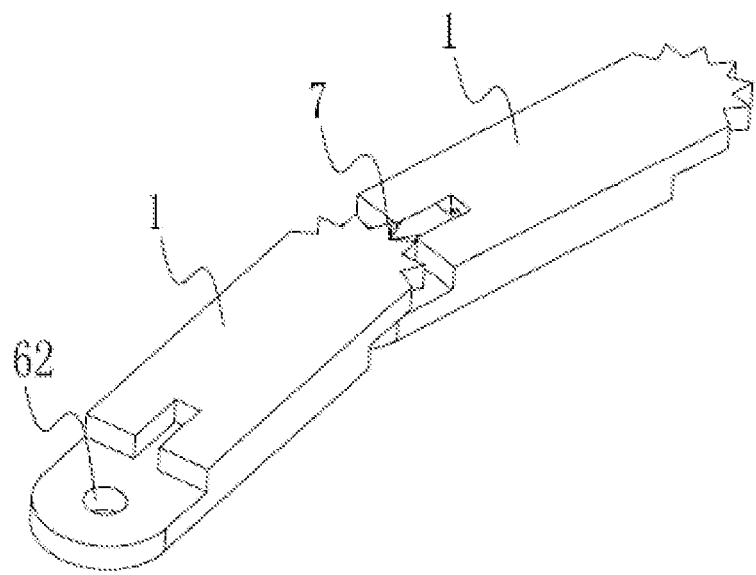
FIGS. 14 and 15 are schematic diagrams showing that the connecting units are pivotally connected by using a ratchet and ratchet wheel as a locking mechanism.
Figure 15:
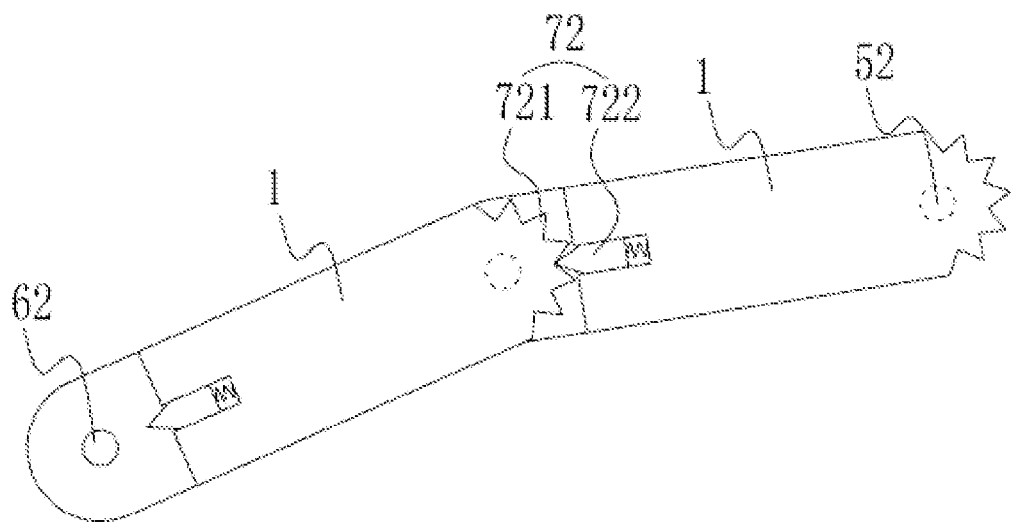

Thirdly, with reference to FIGS. 14 to 19, the corresponding mating structure of the first connecting part 5 and the second connecting part 6 is an articulated connection structure, at which a locking mechanism 7 is provided. Wherein, the corresponding mating structure can be further divided into at least three specific structures according to the difference of articulated connection and the locking mechanism 7:

A. As shown in FIGS. 14 and 15, the corresponding mating structure of the first connecting part 5 and the second connecting part 6 is a pivotal connection structure, which is in running fit with a corresponding rotating shaft 52 and a shaft hole 62, and then locked by a ratchet and ratchet wheel mechanism 72, namely, when rotating relative to each other to the desired angle θ, the two cofferdam baffles 1 are locked by a corresponding ratchet 722 in fit with a ratchet wheel 721; without loss of generality, the ratchet 722 should be a sliding installation structure telescopically controlled, namely, when the ratchet 722 is retracted, the locking fit between the ratchet 722 and the ratchet wheel 721 can be released, and when the ratchet 722 are extended, the ratchet can be in locking fit with the ratchet wheel 721.

Figure 16:
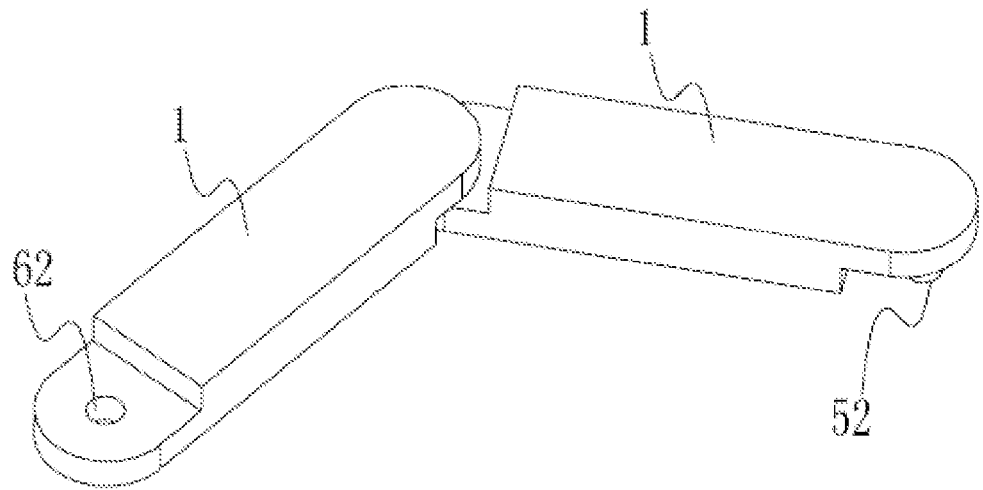
FIGS. 16 and 17 are schematic diagrams showing that the connecting units are pivotally connected by using a screw as a locking mechanism.
Figure 17:
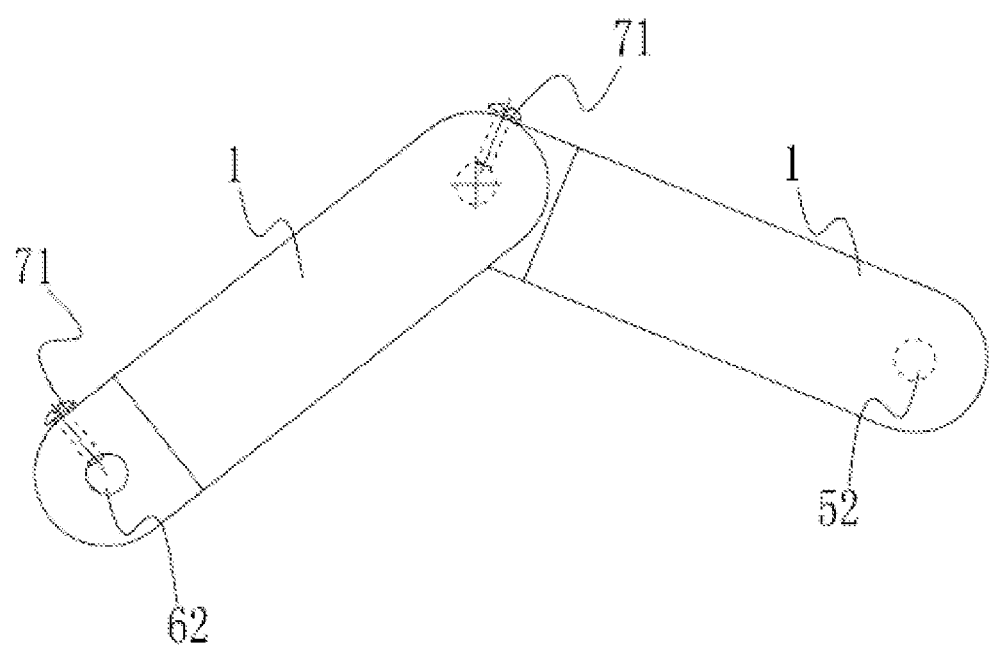

B. As shown in FIGS. 16 to 17, the corresponding mating structure of the first connecting part 5 and the second connecting part 6 is a pivotal connection structure, which is in running fit with the corresponding rotating shaft 52 and the shaft hole 62, and then locked by a screw 71, namely, when rotating relative to each other to the required angle θ, the two cofferdam baffles 1 are locked by tightening the screw 71, and the angle θ can be adjusted simply by loosening the corresponding screw 71.

Figure 4:
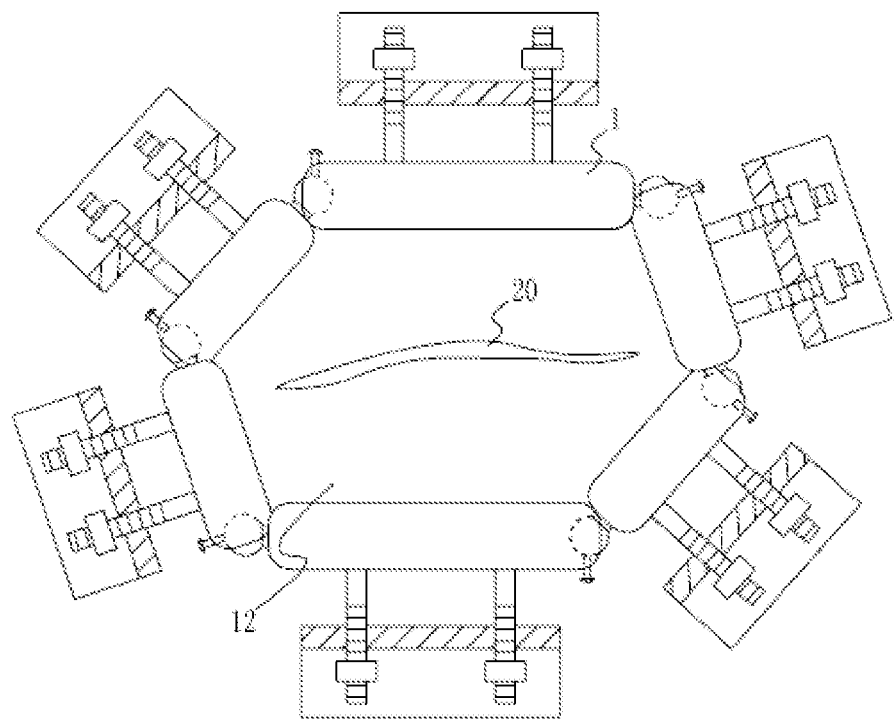
FIG. 4 is a structural representation of a plurality of connecting units connected sequentially in FIG. 1.
Figure 18:
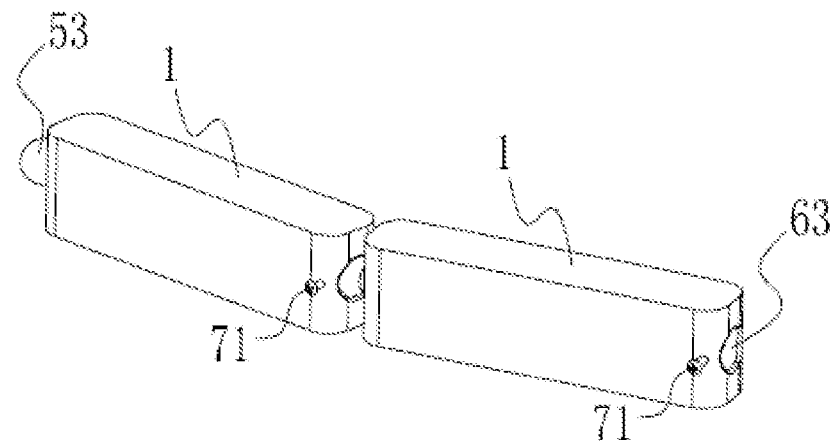
FIGS. 18 and 19 are schematic diagrams showing that the connecting units are of ball joints by using a screw as a locking mechanism.
Figure 19:
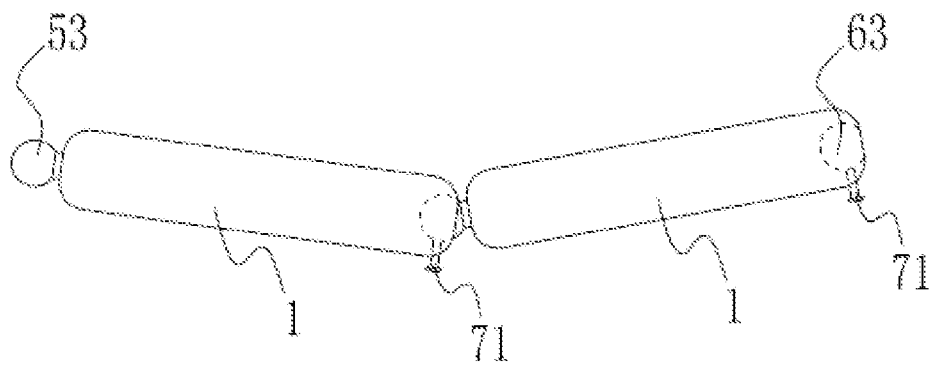

C. As shown in FIGS. 18 to 19, the corresponding mating structure of the first connecting part 5 and the second connecting part 6 is a ball connection structure, which is in running fit with a corresponding ball 53 and a ball cavity 63, and then locked by the screw 71, namely, when rotating relative to each other to the required angle θ, the two cofferdam baffles 1 are locked by tightening the screw 71, and the angle θ can be adjusted simply by loosening the corresponding screw 71. By adopting the ball connection structure, theoretically, the angle θ can be adjusted and locked by means of the adjustment and control of the spatial angle within a certain range. Wherein FIGS. 1 and 4 show a wound closure device formed by the above ball connection structure.

Fourthly, with reference to FIGS. 5 to 10, the limiting connecting rod 8 can be further provided, and the position of the cofferdam baffle 1 can be locked by the limit connecting rod 8 at this time, accordingly, the corresponding mating structure of the first connecting part 5 and the second connecting part 6 should be made into an articulated connection structure; meanwhile, the cofferdam baffle 1 is provided with at least one limiting slot 9 arranged at intervals along the connecting direction of the cofferdam baffle 1; and an end of the limiting connecting rod 8 is provided with a chuck 10 in correspondingly clamping fit with the limiting slot 9. For example, with the structure shown in FIGS. 5 to 7, each of the cofferdam baffles 1 is provided with three limiting slots 9, and corresponding limiting connecting rods 8 are provided to lock positions of the cofferdam baffles 1 relatively. Without loss of generality, when the limiting connecting rod 8 is installed, the limiting connecting rod 8 with corresponding shape and size should be selected as required, on the one hand, to ensure the distance between the cofferdam baffles 1 arranged opposite to each other, and on the other hand, to stabilize the shape of the whole window 12 formed by enclosing the cofferdam baffles. More specifically, with reference to FIG. 7, three or even four cofferdam baffles 1 can be connected at the same time by corresponding Y-shaped or X-shaped limiting connecting rods 8, so as to further stabilize the shape of the window 12.

Without loss of generality, the limiting slot 9 and the chuck 10 can be made into an articulated mating structure or a directional mating structure. The articulated mating structure means that the limiting slot 9 can rotate correspondingly after being matched with the chuck 10, for example, the limiting slot 9 is provided as a cylindrical slot, while the chuck 10 is provided as a cylindrical post. The directional mating structure means that the limiting slot 9 is not allowed to rotate correspondingly after being matched with the chuck 10, for example, the limiting slot 9 is made into a "T-shaped" slot or dovetail slot structure, and the corresponding chuck 10 is made into a corresponding mating structure.

Figure 5:
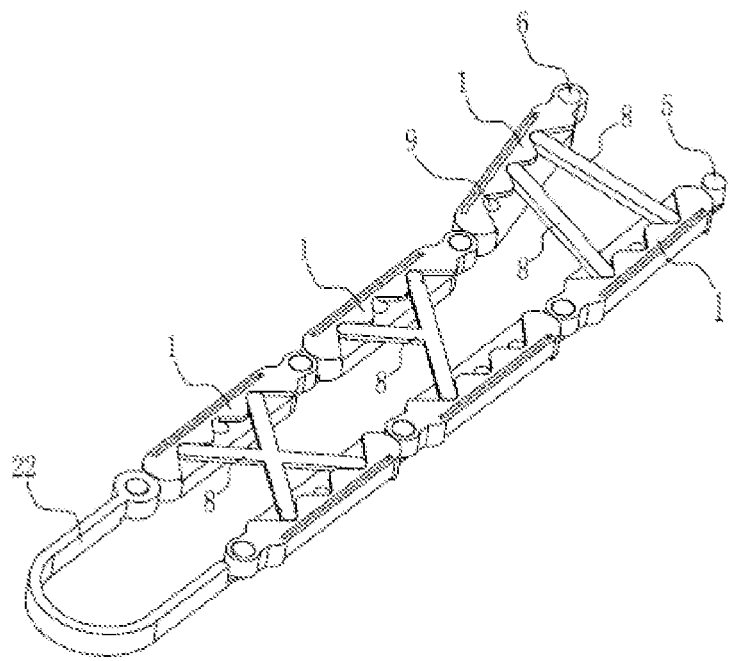
FIG. 5 is a structural representation of a cofferdam baffle partially connected in another connecting unit.
Figure 6:
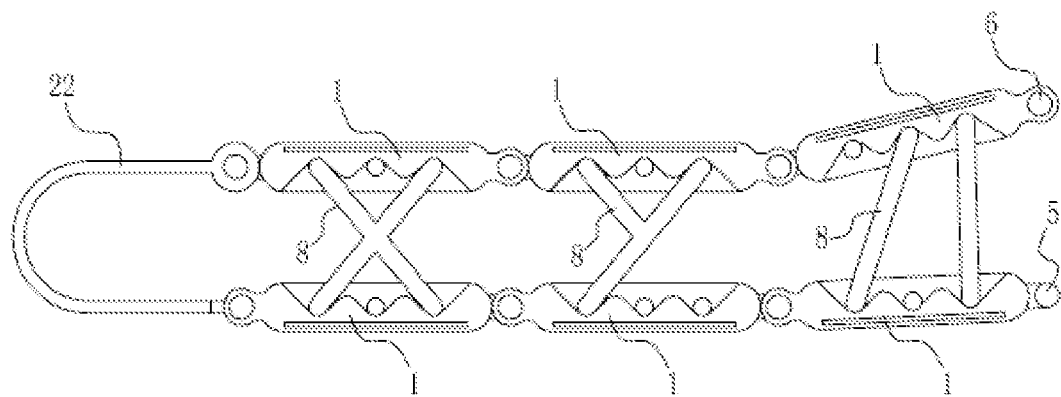
FIG. 6 is a top view of FIG. 5.
Figure 7:
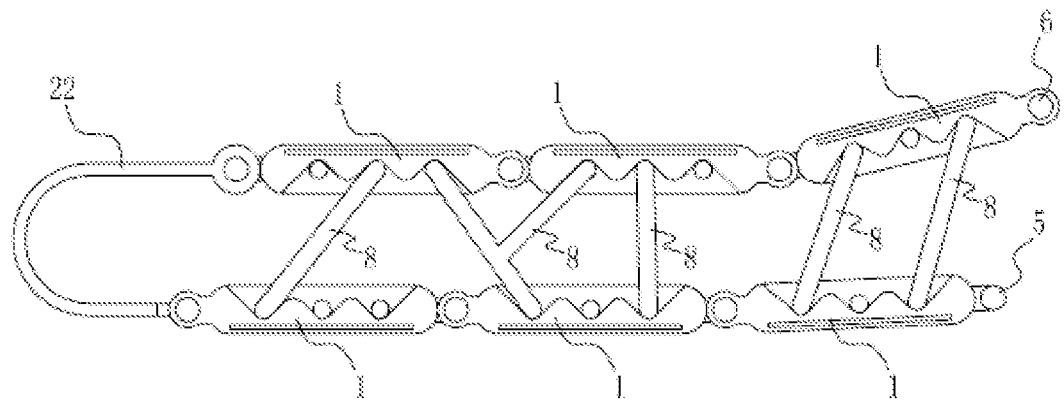
FIG. 7 is a schematic representation of the limiting connecting rods connected alternately in FIG. 6.
Figure 8:
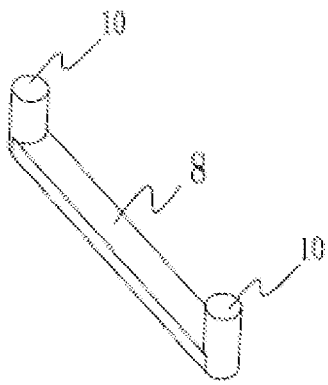
FIG. 8 is an I-shaped limiting connecting rod.
Figure 9:
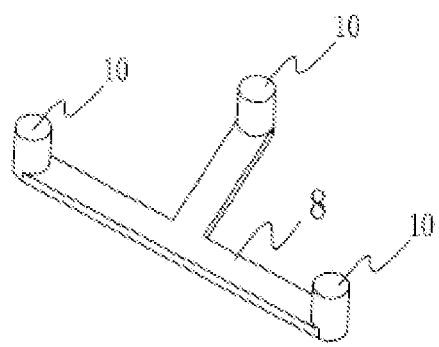
FIG. 9 is a Y-shaped limiting connecting rod.
Figure 10:
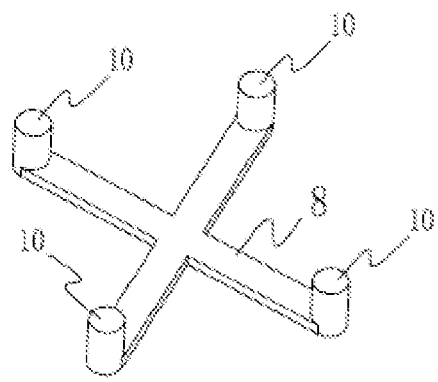
FIG. 10 is an X-shaped limiting connecting rod.

In addition, when the limiting slot 9 and the chuck 10 can be made into an articulated mating structure, the limiting connecting rods 8 can be of I-shaped, Y-shaped or X-shaped in the present invention, and the limiting connecting rods 8 can be matched with the above three shapes at the same time for selective use, as shown in FIGS. 8 to 10. At this time, when the two opposite cofferdam baffles 1 need to be connected and locked by the limiting connecting rod 8, if only one I-shaped limiting connecting rod 8 is used, both cofferdam baffles 1 can rotate around the connection point at the chuck 10 correspondingly; when only one Y-shaped limiting connecting rod 8 is used, only one cofferdam baffle 1 can rotate around the connection point at the chuck 10 correspondingly, while the other cofferdam baffle 1 cannot rotate relatively; when an X-shaped limiting connecting rod 8 is used, the positions of two cofferdam baffles 1 can be fixed and locked. With such an arrangement, the position relationship and the assembled shape of the cofferdam baffle 1 can be adjusted more conveniently, so as to better match with the actual shape of a wound 20. Without loss of generality, in specific use, different positions can be connected by corresponding I-shaped, Y-shaped or X-shaped limiting connecting rods as required, for example, as shown in FIGS. 5 to 7, I-shaped, Y-shaped or X-shaped limiting connecting rods 8 are adopted at the same time.

More specifically, in order to facilitate the installation of the limiting connecting rod 8, one end of the limiting slot 9 can further penetrate through an upper end of the cofferdam baffle 1 in the present invention.

Figure 2:
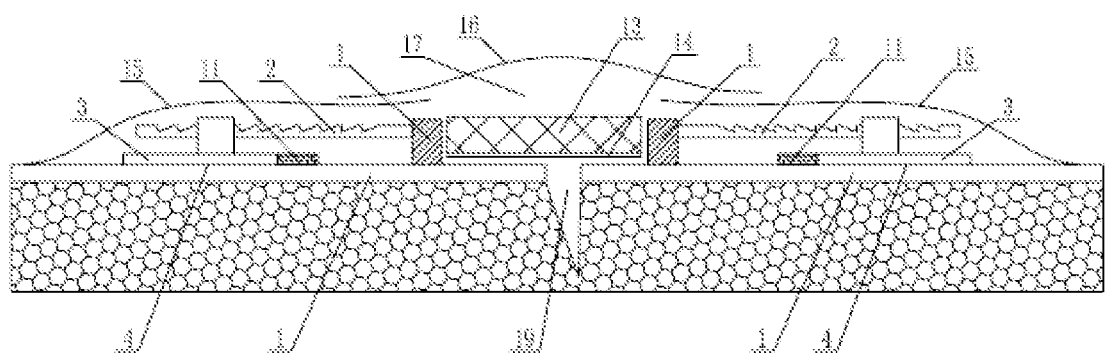
FIG. 2 is a schematic diagram of the closure device with a ratchet structure.
Figure 3:
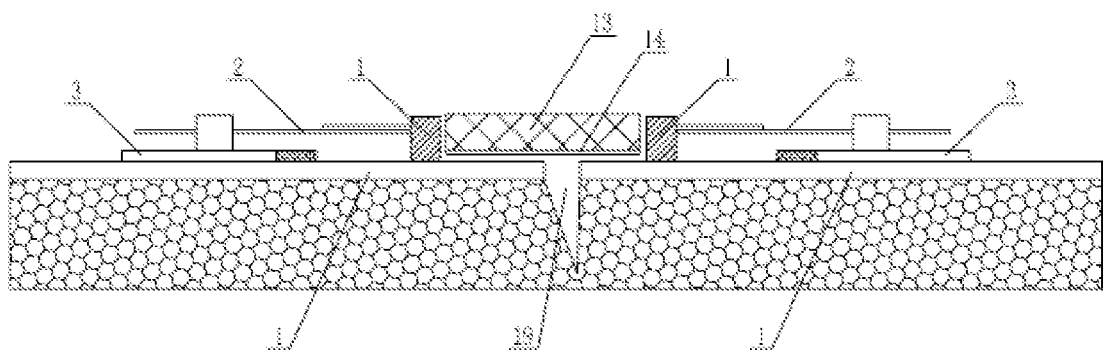
FIG. 3 is a schematic diagram of the closure device with a lacing structure.

The closure device 2 described in the present invention is used for generating a closure force between the cofferdam baffle 1 and the fixator 3, so as to close and align the wound 20, which is beneficial to the healing and subsequent treatment of the wound. The fixator 3 described in the present invention is used for attaching to skin 19 around the wound 20, specifically, the fixed adhesive surface 4 is affixed to the skin 19 around the wound 20, as shown in FIGS. 2 and 3.

More specifically, the closure direction of the closure device 2 is preferably perpendicular to the cofferdam baffle 1 in the present invention so that the closure device 2 can apply a closure force to the cofferdam baffle 1. Moreover, in order to ensure that the closure force of the closure device 2 on the cofferdam baffle 1 is relatively evenly distributed, a plurality of closure devices 2 can be provided in each connecting unit and arranged at intervals along the connecting direction of the cofferdam baffle 1, for example, as shown in FIG. 11, two closure devices 2 are provided. In addition, the closure device 2 in the present invention can also specifically adopt the ratchet structure or the lacing structure disclosed in Document 1, which will not be detailed herein; certainly, without loss of generality, the closure device 2 of the present invention can also adopt other structures with a closure effect. Furthermore, a base band 11 parallel to the cofferdam baffle 1 is further provided on the edge of the fixator 3 facing the side of the cofferdam baffle 1; wherein, the base band 11 should be a rigid linear skeleton, the skin 19 on the edge side of the wound 20 can be pulled evenly and parallelly through the base band 11 to close to the wound midline, the structure of the base band 11 is the same as disclosed in Document 1, and will not be detailed herein.

The wound closure device of the present invention is formed by combining the connecting units, wherein a plurality of the connecting units need to be provided, and the connection ends of the cofferdam baffles 1 in the plurality of connecting units are sequentially connected and enclosed to form an annular closed window 12, with the closure device 2 and the fixator 3 in each connecting unit located at the periphery of the window 12. In the specific example shown in FIGS. 1 and 3, six connecting units are connected sequentially through a cofferdam baffle 1 and enclosed to form a corresponding window 12; as shown in FIGS. 5 to 7, corresponding connecting units are connected to form a partial structure of one end of the wound closure device.

Without loss of generality, the connecting unit in the present invention can have various sizes, which provides flexible options according to use needs, the lengths of the cofferdam baffles 1 in connecting units with different sizes can be set to different values, for example, in FIG. 1, the cofferdam baffles 1 of two connecting units located at upper and lower positions are obviously longer than those at left and right positions.

In the present invention, the connection mating structure between two adjacent cofferdam baffles 1 is able to adjust and lock the connecting angle θ, therefore, when assembling a wound closure device, the corresponding number and size of connecting units can be selected according to the shape and size of an actual wound 20, and the wound closure device adapted to the actual wound 20 can be finally formed by adjusting the connecting angle θ between the cofferdam baffles 1 to ensure effective enclosure and isolation of the wound 20.

In addition, when the window 12 is formed, for the convenience of a closed connection of the window 12 at both ends along the direction of a wound, a U-shaped part 22 can be further provided, as shown in FIGS. 5 to 7. The U-shaped part 22, through which a corresponding bending structure can be formed straightly, can be composed of a U-shaped cofferdam baffle, so that a single U-shaped part 22 can substitute two connecting units and a connection structure there between; furthermore, the U-shaped part 22 is capable of forming a bending structure with a relatively fixed angle, equivalently, the connecting angle θ between the cofferdam baffles 1 in the two connecting units is a fixed value, thus avoiding the necessity to connect and adjust the connecting angle θ between the cofferdam baffles 1 by means of "the first connecting part 5 and the second connecting part 6 being corresponding mating structures capable of adjusting and locking the connecting angle θ" when the two connecting units are connected. Certainly, without loss of generality, when U-shaped part 22 is used, the first connecting part 5 and the second connecting part 6 should be correspondingly arranged on the U-shaped part 22 since the two ends of U-shaped part 22 need to be connected to the cofferdam baffle 1 of the connecting unit at the corresponding end, moreover, the outer side of the U-shaped part 22 can be provided with or without a closure device 2 and a fixator 3, as the case may be.

Without loss of generality, affected by the closure effect of the closure device 2, the cofferdam baffle 1, the U-shaped part 22, or the like in the present invention should have certain structural strength, and can be specifically used as relatively hard structural parts, for example, relatively hard plastic injection parts.

More specifically, the wound closure device described in the present invention can also be provided with corresponding functional modules within the internal space of the window 12, which are some of the supplies commonly used in the treatment of wounds, including but not limited to the following modules: an alignment reference support module 13, a wound exudate absorption module, a wound hemostasis module, a wound bacteriostasis and antibacterial module, a wound information acquisition module and a cell tissue regeneration module. The functional modules mentioned above are also described in Document 1, and will not be detailed in the present invention. Wherein, the alignment reference support module 13 is placed inside the window 12, and a bottom surface, facing the wound, of the alignment reference support module is provided as a rigid reference plane 14, as shown in FIGS. 2 and 3, which can better define the rigid reference plane 14 in the vertical direction, and allow a front side thereof to press against a wound to ensure that the skin edge of the wound is aligned and flat in the vertical direction.

In addition, in the present invention, a peripheral sealing film 15 and an internal sealing film 16 are further provided, wherein the peripheral sealing film 15 correspondingly covers the periphery of the window 12 and is provided with an opening 21 corresponding to the window 12, the internal sealing film 16 correspondingly covers the window 12, and the edge of the internal sealing film 16 fits over an edge corresponding to the opening 21 of the peripheral sealing film 15 in a sealing manner, so as to form a negative pressure sealing chamber 17 in an area covered by the peripheral sealing film 15 and the internal sealing film 16. By providing the peripheral sealing film 15 and the internal sealing film 16, the outer peripheral edge of the peripheral sealing film 15 is affixed to the skin 19 in a sealing manner to form a corresponding negative pressure sealing chamber 17, which can be evacuated to generate pressure through the corresponding sealing film, for one thing, a negative pressure condition is created in an area corresponding to the wound 20 to meet the treatment requirements such as rinsing and cleaning of the module or the built-in dressing in the window 12, for another, through negative pressure, the built-in functional modules or built-in alignment reference support module 13 and the rigid reference plane 14 under the sealing film, the rigid reference plane 14 is tightly fixed to skin surface and free skin edge of a wound at zero distance, allowing the original and amorphous free skin edge of the wound to be tightly fixed to the rigid reference plane 14 in the vertical direction, relying on the rigid reference plane 14 to force the free skin edge of the wound to be aligned and leveled, ensuring that the functional module built in the wound is effectively located above the wound to be treated.

More specifically, in order to facilitate the evacuation of the negative pressure sealing chamber 17, a negative pressure pipeline 18 may be further provided, and the negative pressure pipeline 18 connects the negative pressure sealing chamber with the outside. When necessary, a one-way valve can be provided on the negative pressure pipeline 18, so as to allow operations such as vacuum suction or change of the washing and cleaning liquid in the cavity for many times as required. Certainly, under the condition that the negative pressure pipeline 18 is not provided, when vacuumizing the negative pressure sealing chamber 17, a pipe should be stretched into the sealing chamber from the edge of the sealing film, and after vacuumizing, the pipe is quickly removed and the edge of the sealing film is sealed to avoid air leakage.

The invention claimed is:

1. A connecting unit, comprising: a cofferdam baffle, a closure device and a fixator, one end of the closure device being connected to the fixator and the other end thereof being connected to the back side of the cofferdam baffle, a fixed adhesive surface for attaching to skin being provided on the bottom surface of the fixator, left and right ends of the cofferdam baffle being connecting ends, a first connecting part being arranged at one connecting end of the cofferdam baffle and a second connecting part being arranged at the other connecting end thereof, the first connecting part and the second connecting part being corresponding mating structures capable of adjusting and locking the connecting angle θ.

2. The connecting unit according to claim 1, wherein the first connecting part is a polygonal prism and the second connecting part is a polygonal hole consistent with the polygonal prism.

3. The connecting unit according to claim 1, wherein the corresponding mating structure of the first connecting part and the second connecting part is an articulated connection structure, at which a locking mechanism is provided.

4. The connecting unit according to claim 1, further comprising a limiting connecting rod, the corresponding mating structure of the first connecting part and the second connecting part being an articulated connection structure, the cofferdam baffle being provided with at least one limiting slot arranged at intervals along the connecting direction of the cofferdam baffle, and an end of the limiting connecting rod being provided with a chuck in correspondingly clamping fit with the limiting slot.

5. The connecting unit according to claim 4, wherein the limiting slot and the chuck are of an articulated mating structure, and the limiting connecting rod one of I-shaped, Y-shaped, and X-shaped.

6. The connecting unit according to claim 4, wherein the limiting slot and the chuck are of a directional mating structure.

7. The connecting unit according to claim 1, wherein the closure direction of the closure device is perpendicular to the cofferdam baffle, a plurality of closure devices are provided, the plurality of closure devices are arranged at intervals along the connecting direction of the cofferdam baffle, the closure device has one of a ratchet structure and a lacing structure, and a base band parallel to the cofferdam baffle is provided on the edge of the fixator facing the side of the cofferdam baffle.

8. A wound closure device formed by combining a plurality of the connecting units according to claim 1, such that a plurality of connecting units are provided, and the plurality of connecting units are sequentially connected through the connecting ends of the cofferdam baffle and then enclosed to form an annular closed window, wherein the closure device and the fixator in each of the connecting units are located at a periphery of the window.

9. The wound closure device according to claim 8, wherein functional modules are provided within an internal space of the window and are at least one of an alignment reference support module, a wound exudate absorption module, a wound hemostasis module, a wound bacteriostasis and antibacterial module, a wound information acquisition module and a cell tissue regeneration module, and a bottom surface, facing a wound, of the alignment reference support module has a rigid reference plane.

10. The wound closure device according to claim 8, further comprising a peripheral sealing film and an internal sealing film, the peripheral sealing film correspondingly covering the periphery of the window, an opening of the peripheral sealing film corresponding to the window being arranged on the peripheral sealing film, the internal sealing film correspondingly covering the window, and the edge of the internal sealing film fitting over an edge corresponding to the opening of the peripheral sealing film in a sealing manner, so as to form a negative pressure sealing chamber in an area covered by the peripheral sealing film and the internal sealing film.

11. The connecting unit according to claim 1, wherein the first connecting part is a plurality of positioning posts and the second connecting part is a plurality of positioning holes in fit with the positioning posts in a misaligned manner.

* * * * *